United States Patent
Hermansson et al.

(10) Patent No.: US 8,778,377 B2
(45) Date of Patent: Jul. 15, 2014

(54) DRUG IMPLANT CARRIER FOR DRUG DELIVERY

(75) Inventors: Leif Hermansson, Tönnes väg (SE); Håkan Engqvist, Margaretavägen (SE)

(73) Assignee: Doxa AB, Uppsala (SE)

( * ) Notice: Subject to any disclaimer, the term of this patent is extended or adjusted under 35 U.S.C. 154(b) by 1143 days.

(21) Appl. No.: 12/040,068

(22) Filed: Feb. 29, 2008

(65) Prior Publication Data

US 2008/0213337 A1 Sep. 4, 2008

Related U.S. Application Data

(60) Provisional application No. 60/904,183, filed on Mar. 1, 2007.

(51) Int. Cl.
- A61K 47/02 (2006.01)
- A61F 2/02 (2006.01)
- A61C 5/00 (2006.01)

(52) U.S. Cl.
USPC .................. 424/423; 514/770; 433/228.1

(58) Field of Classification Search
None
See application file for complete search history.

(56) References Cited

U.S. PATENT DOCUMENTS

| | | | |
|---|---|---|---|
| 5,549,123 A | | 8/1996 | Okuyama et al. |
| 5,968,253 A | * | 10/1999 | Poser et al. .................. 106/691 |
| 6,860,932 B2 | * | 3/2005 | Oshida ........................ 106/35 |
| 7,244,301 B2 | | 7/2007 | Axen et al. |
| 2006/0156959 A1 | | 7/2006 | Engqvist et al. |
| 2007/0232704 A1 | | 10/2007 | Axen et al. |
| 2007/0233213 A1 | | 10/2007 | Axen et al. |

FOREIGN PATENT DOCUMENTS

| | | | |
|---|---|---|---|
| EP | 1 795 171 | 6/2007 | |
| WO | 0176535 | 10/2001 | |
| WO | WO 01/76535 | * 10/2001 | ............... A61K 6/06 |
| WO | WO 2004/058194 | 7/2004 | |

OTHER PUBLICATIONS

Lars Kraft, "Calcium aluminate based cement as dental restorative materials", Comprehensive Summaries of Uppsala Dissertations from the Faculty of Science and Technology vol. 775, Uppsala 2002, pp. 1-67.
International search report in corresponding PCT/SE2008/050233.
Krajewski, a. et al., "Porous ceramic bodies for drug delivery", *Journal of Materials Science Materials in Medicine*, vol. 12, (2000), pp. 763-771.
Lasserre, A. et al., "Ceramic drug-delivery devices", *Critical Reviews in Therapeutic Drug Carrier Systems*, 15(1) 1-56 (1998).

* cited by examiner

*Primary Examiner* — Dennis Heyer
(74) *Attorney, Agent, or Firm* — Young & Thompson

(57) ABSTRACT

The present invention relates to ceramic precursor material exhibiting injectability and properties that make the material suitable as a carrier material used in drug delivery. According to the invention this is accomplished by selecting a microstructure based on pre-reacted phases and after injection established phases, which contain anti-infective and/or anti-inflammatory drugs. The present invention also relates to a cured ceramic material and a method of manufacturing said cured material. The precursor and the cured ceramic material according to the present invention can suitably be used for filling orthopaedic cavities and other bone voids.

30 Claims, 1 Drawing Sheet

DRUG IMPLANT CARRIER FOR DRUG DELIVERY

THE FIELD OF THE INVENTION

The present invention relates to combined ceramics implant and drug carrier for drug delivery. The implant material comprises chemically bonded ceramics (un-hydrated, and/or partly hydrated and/or fully hydrated). The materials properties make the materials suitable as carrier material for different types of drugs. The properties of the material make it suitable as an implant. The invention relates also to a method for producing an implant carrier material loaded with a drug. The carrier can work as a stable or resorbable implant. The present invention further relates to a ceramic precursor material that is injectable.

BACKGROUND

Carrier materials for drug delivery are found within a broad range of materials, polymers, metals and ceramics.

General aspects of ceramics for use in drug delivery of drugs are given in by Ravaglioli et al. in *J Mater Sci Mater Med.* 2000 11(12):763-71 and by Lasserre and Bajpaj in *Critical Reviews in Therapeutic Drug Carrier Systems*, 15,1 (1998).

In a number of related patents and patent applications the use of Chemically Bonded Ceramics (CBC) (such as sulphates, phosphates, silicates and aluminates), especially the use of Ca-aluminate based materials (CA) has been proposed as implant materials within odontology and within orthopaedics, but also as carrier systems for drug delivery.

Biocompatible cements based on calcium aluminate are e.g. described in the patent application "U.S. Pat. No. 7,244, 301 Heat generating biocompatible ceramic materials", claiming priority from SE-0202895-9, filed Sep. 30, 2002. This document describes an implant material for use as a carrier material in drug delivery. Another related patent application "WO2004058194 Chemically bonded biomaterial with tailored properties" has been published. Said application discloses a biomaterial for use in drug delivery.

In EP1795171 A1 "Powdered GBC system with improved reaction feature" the use of the system as a carrier is also presented.

In view of the prior art ceramic compositions, there is a need for a carrier material for drug delivery that exhibits improved safety of the drug delivery system with regard to a) how the drug is incorporated, b) where it is released, and c) how the drug is released.

An implant for use in drug administration should meet the above mentioned criteria and must also take account of and control the setting and curing reactions in vitro and in vivo, as well as to control the porosity of the finally cured material and use of additives, and processing agents, to assure an optimal microstructure.

BRIEF DESCRIPTION OF THE INVENTION

The present invention provides implant materials based on ceramics, more specifically chemically bonded ceramics (CBC) and that exhibit well-controlled microstructure for controlled and safe drug delivery.

According to one aspect, the present invention relates to an optimised injectable material as a carrier material for drugs in drug delivery, and how said material is introduced in the body via an injection system or a paste including a water-based hydration liquid. The invention deals with a minimally invasive introduction of the drugs, encapsulated by the carrier material, by injection directly into the body.

The present invention relates to both a ceramic precursor powder material and a cured ceramic material that at least in part have been made from said precursor material.

The carrier material according to the invention describes an optimised material for drug delivery take into account these factors, 1) the chemical composition of the carrier material, 2) the injectability, and 3) the microstructure of the carrier material to ensure a controlled release of the drug, 4) type of medical agents.

The precursor powder material consumes much water or water-based hydration liquid during, the curing of the carrier material. The precursor powder material may also include secondary phases such as hydrated CBC and/or other porous granules, and radio-opaque particles. The latter material may be used to be able to follow exactly where the injectable carrier is placed. The developed/selected microstructure in the material will allow for a release rate suitable for different drugs.

Before hardening, the carrier material according to the present invention exhibits a high degree of mouldability, including injectability. They are thus particularly useful for site-specific placement of the drug. The carrier chemistry allows for loading of almost any medical agent. The drugs can favourably be loaded into the pore system of inert filler particles, mixed with the powdered binder phase, aqueous liquid or processing agents (accelerators, retarders, viscosity controlling agents and other rheological agents), or a combination of them.

The carrier may for example be used as a vehicle for transport and delivery of the medical agents including drugs (pain relief, vascular treatment, bone restoration and activation of drugs), a load-bearing bone graft material loaded with bone-active materials (for example an implant in the cortical bone), a material substituting skeleton parts after that tumours have been removed, i.e. as part in cancer treatment, an injectable implant material, an augmentation material for lost body tissue, and a paste introduced at the same time as another load-bearing implant. The carrier implant may for example be implanted by direct injection, or by mini-invasive surgery.

Thus drugs can be loaded both during formation of hydrates and/or after hydration by infiltration (partly hydrated or fully hydrated) materials are used. For hydrophobic medical agents, the agent is preferably mixed in the precursor powder and/or together with a second ceramic filler (if inhomogenity is to be prevented). When loaded in the precursor material, the drug will after hydration be very well distributed between the formed nano-hydrated crystals.

The present invention also relates to the precursor powder, the hydration liquid, a kit comprising the ceramic precursor powder and hydration liquid, and the cured ceramic material, as well as to the use of these for orthopaedic and dental applications, and drug delivery.

The advantage with the disclosed ceramic material is that it can have a dual function as an implant and as a carrier for drugs for site-specific drug release.

The present invention further relates to a method of manufacturing said cured material, and bioelements, medical or orthopaedic implants, a dental filling material or dental implant, a carrier material, or a drug carrier, as well as to the products produced therefrom.

DETAILED DESCRIPTION OF THE INVENTION

Figure 1:
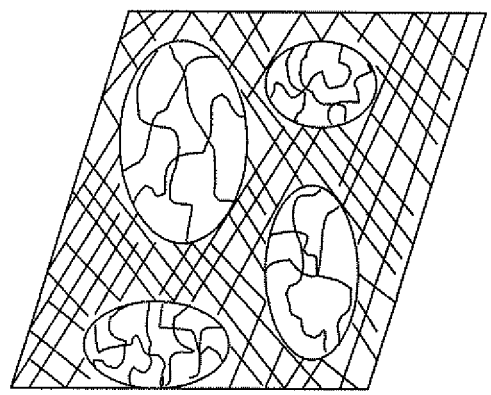
FIG. 1 shows a schematic representation of the microstructure of a cured ceramic material according to the present invention.

The precursor powder cures as a result of hydration reactions, between a ceramic oxide powder, primarily based on Ca-silicates and/or Ca-aluminates, and water. Through the hydration, new phases of hydrates are formed, which to a great part establish the microstructures needed to control the release of drugs incorporated, in the injectable precursor material.

The drug may be introduced into precursor and/or the hydrated CBCs and/or other porous phases (such as inert filler particles) prior to the establishment of the injectable material.

The injectable material is formed into a paste by mixing it with a water-based hydration liquid, which is then ready to be injected. Directly after the injection, the paste starts to develop the final microstructure that to a great extent will contribute to the controlled release of the drug.

Said water-based liquid may also comprise viscosity-controlling additives selected from one or more of carboxylic acids, polymerised carboxylic acids, thickening agents, superplasticisers. These may be mixed with the drug before preparation of the final injectable paste.

Drugs and/or other medical agents which favourably may be delivered using the carrier according to the present invention are therapeutic agents and/or anti-infective and/or anti-inflammatory drugs.

The drug can be of any kind. Suitable drugs may be chosen from pain relief drugs, antiphlogistics, drugs for cancer/tumour treatment, vascular treatment, bone restoration, antibacterial and anti-inflammatory agents, antifungal agents, antivirus agents, analgesics, anticonvulsants (e.g., propantheline bromideatropine sulfate, oxitropium bromide, timepidium bromide, scopolamine butylbromide, trospium chloride, butropium bromide, N-methylscopolamine methyl sulfate and methyloctatropine bromide); bronchodilators (e.g., theophylline, aminophylline, sodium cromoglicate); antidepressants, auto-immune disorder and immunological disease agents, hormonal agents, TGB-beta, morphogenic protein, trypsin-inhibitor, osteocalcine, calcium-binding proteins (BMP), growth factors, Bisphosphonates, vitamins, hyperlipidemia agents (e.g., pravastatin sodium and fluvastatin sodium); sympathetic nervous stimulants (e.g., dihydroergotamine mesilate and isoproterenol hydrochloride, etilefrine hydrochloride); oral diabetes therapeutic drugs (e.g., glibenclamide, tolbutamide and glymidine sodium); oral carcinostatics (e.g., marimastat); contrast materials, radiopharmaceuticals, peptides, enzymes, vaccines and mineral trace elements or other specific anti-disease agents, as well as combinations of said drugs.

The list is riot limited to the medicaments above.

The incorporation of the drugs or medical agents into the carrier material may be performed by filling the pores of the precursor powder with said agents, by simply mixing it with the powder prior to mixing it with the hydration liquid, or mixing it with the hydration liquid (or with any additives) prior to mixing it with the precursor powder. Depending on the type of drug delivery for which the carrier material is intended, a combination of one or more of said techniques may be used.

The carrier material may further comprise one or more of other hydrated or non-hydrated hydraulic phases, such as calcium aluminates, calcium silicates, calcium phosphates, calcium sulphates and Portland cement, as well as hydroxyapatite.

Optionally, it may also comprise inert phases of oxides, such as Ti, Si and/or Zr, in order to increase the radio-opacity, if said property is desired. The oxides may take the form of porous and/or dense particles.

The properties of the implant/carrier material may be broadly controlled. To achieve suitable properties, the characteristics of the ingredients should be kept under control. The following properties are according to the present invention of uttermost significance;

a) Type of ceramic precursor for producing the chemically bonded ceramic
b) Grain size distribution of the precursor powder particles
c) Granule size of additive granules
d) Microstructure of the porous particles for drug incorporation
e) Microstructure of material during and after injection
f) Setting and curing time
g) pH-control
h) General resorption rate of the carrier material
i) Total amount of water in the injectable material
j) The amount of water which is consumed in the curing reactions
k) Additives to ensure an appropriate radio-opacity Type of Chemically Bonded Ceramic The preferred chemical compositions, with an inherent property profile to meet all the features described in the present invention, are those based, on chemically bonded ceramics, which during hydration consume much water. The only systems available are those based on aluminates and silicates (i.e. consume a great amount of water). Phases such CA, C3A and C12A7 and C3S (CA and CS=cement terminology for calcium aluminates and calcium silicates, respectively) may be used. The Ca-aluminate phases may be used as separate phases, or as mixtures of phases. When C3S is used, it may advantageously be combined with a Ca-aluminate phase. The above-mentioned phases, all in non-hydrated form, act as the binder phase in the carrier material when hydrated. The CA-carrier materials are stable materials, while the CS-materials are slowly resorbable materials.

Grain Size Distribution

The grain size of the precursor powder particles may be below 5 micrometers. This is to assure a rapid hydration. When the material is injected as described in smaller quantities (<2 ml), the exothermic reactions of the chemically bonded ceramics are compensated by the improved contact with the surrounding body tissue due to a high hydrophilicity of the paste material, resulting in diffusion and direct cooling. The thermal properties of the carrier material, especially heat conductivity, are similar to those of body tissue.

Granule Size

To increase the homogeneity and the injectability of the paste, the precursor materials (i.e. the CBCs and the hydrated CBCs and additives) should be in granular form with a size (determined as the average diameter) less than 500 micrometers, preferably in the interval of 100-300 micrometers.

Microstructure of the Porous Precursor Particles for Drug Incorporation

The microstructure of the additives which are penetrated by/loaded with the active medical agent is primarily characterised by its porosity, which should be an open porosity in the interval of 10-40 volume-%. The average pore size determined by Hg-porosimetry should be in the interval of 0.01-5 micrometers, see FIG. 1.

Examples of additives according to the present invention include hydrated CBCs including Ca-sulphates and Ca-phosphates, and oxides.

Microstructure of Material during and After Injection

Additional porosity is generated during the hydration of the CBCs. Said porosity, which is open, is suitably be in the interval of 10-25 vol-%. The average pore canal size (i.e. the diameter of the pores formed between the particles of the hydrated material) is normally be less than 10 nanometers. The crystal size of the formed CBC hydrates is approximately 20-50 nanometers. See. FIG. 1.

In FIG. 1, the round or elliptically depicted elements represent the inert porous particles with pore size of 0.01-5 micrometers, whereas the hatched areas represent grains of cured hydrated material (having a crystal size of 20-50 nanometers) with pore canal openings of less than 10 nanometers.

Figure 2:
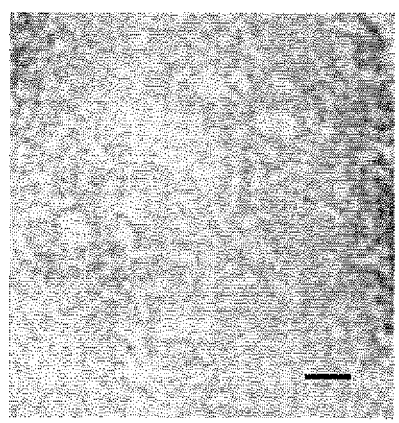
FIG. 2 shows the general hydrated microstructure with nano crystals in the form of a STEM photo. (Bar=50 nm)

FIG. 2 shows a STEM photo of the hydrated phase, where individual hydrated phases are within the interval 10-50 nm. The example shows hydration, of a mono-Ca-aluminate after 24 hrs. The open porosity was 10%. However, the nano-sized pore channels between the hydrated crystals were estimated to be 1-2 nm in width.

Setting Time and Temperature

The setting time should be relatively short, below 30 minutes, and suitably in the interval of 2-10 minutes. The temperature is selected to produce controlled microstructure. The carrier materials are suitably hydrated at a temperature above 30° C., since this yields more stable hydrates in the materials and thus a more stable material. The curing before; loading and/or before introduction of the material into the body can be done in water and/or in an environment with high relative humidity (>60%). The setting and curing times and temperatures are of specific relevance from the viewpoint a ceramic implant material's.

pH-Control

For medical agents sensitive to pH, the pH should be controlled in order to maintain their activity. A suitable pH is normally in the interval of 5-9. This is achieved by introduction of buffer systems. The buffer systems may be based on hydrogen phosphates, and/or acid salts. Said buffer system may Be included in the precursor powder or the hydration liquid, or both.

General Resorption Rate of the Carrier Material

In one embodiment of the invention the carrier material is composed of resorbable CBCs. These are based on silicate and additives of phosphates or sulphates.

Total Amount of Water in the Injectable Material

The amount of water in the injectable material, i.e. the paste, should be in the interval of 30-50 vol-%. Lower contents (<30%) yield a non-injectable material, and whereas higher contents (>50%) yield a paste that is, not controllable during injection, and the cured material will exhibit a non-desirable degree of porosity.

The amount of water Which is Consumed in the Curing Reactions

The water to cement ratio should be in the interval of 0.20-0.50 to assure a complete hydration of the precursor cement or a w/c ratio with a deviation of at most +/−10% from the amount required for total consumption. Excess water favours complementary porosity of the size lager than that formed by the hydrates, as does hydration in moisture at relative humidity >60%.

Additives to Ensure an Appropriate Radio-Opacity

The CBC selected according to the present invention yields by itself a radio-opacity suitable for injection into soft body tissue (such as muscle tissue). In one embodiment of the invention, in order to impart a high radio-opacity, additives with a high density is added for injection into hard body tissue (such as bone tissue). These are favourably biocompatible phases. Examples of such phases are $ZrO_2$ and Sr- and Ba-containing glasses.

Other Additional/Secondary Phases

Optionally, other additives may also be added. These may include hydrates and oxides, which could be both stable or resorbable.

The combination of the material according to the present invention as carrier and implant material make site-specific placement of drugs and implants possible. How the precursor material is produced is described in Example 1.

In summary, the release time is controlled mainly by the contents of the hydrated Ca-based cement phases, the higher the content of the cement, the longer the release time. See Example 2. The optimised (longest) release time is achieved for the hydrated phases with a water content close to the w/c required for complete hydration of the precursor Ca-aluminate or Ca-silicate. By introducing the optional additives, or by changing the w/c ratio, the release time can be controlled from a few hours to more than one day. The release time is also dependant upon where the drug is placed. In cortical bone with limited and slow circulation of body liquid, a release time of months seems possible. Using the mixed cement powder and an inert phase opens up for use of combined drugs, e.g. one for rapid release (based on the inert phase) and the other for slow release (based on the cement phase).

EXAMPLES

Example 1

The release time is strongly related to the microstructure of the carrier used. There are some important ways according to this invention, which are exemplified below.

The Ca-aluminate as well as the Ca-silicate systems include several intermediate phases. The pure aluminate and silicate phases are not available on the market.

The controlled porosity development requires a well-defined phase composition. The sintering time and temperature for achieving CA and C3S are shown in Table 1.

TABLE 1

Synthesis data for Ca-aluminate and Ca-silicate phases

| Phase obtained | Sintering temperature, ° C. | Sintering time, (h) |
|---|---|---|
| CA | 1400 | 4 |
| C3S | 1375 | 5 |

The hydration temperature should preferably exceed 30° C. to achieve the desired phases (the best result). In the experiment the particle size was close to 3 micrometer in average particle size. The particle size of the CBCs was obtained by jet milling, and the particle size distribution was determined by Malvern Mastersize 2000. The phases obtained after 4 hours of hydration were katoite and gibbsite in the CA-system and an amorphous phase and Tobermorite in the CA-system. The w/c ratio used were 0.44 for both systems. The phase analysis was conducted using traditional X-ray diffraction.

Example 2

In the following example it is presented how the materials in example 1 can be used as carriers for drug delivery yielding slow release close to a constant release rate. The compositions used in more details are summarised in Table 2. The test drug was a tartaric compound, N,N,6-trimethyl-2-p-tolylimidazo[1,2-a]pyridine-3-acetamide L-(+)-tartrate (2:1), but could be any other drug could be used. The hydrating liquid was destilled water. In the CA-case the following process agents were used; 0.15% LiCl as an accelerator and 3% Methyl-cellulose (for reasons of viscosity). For CS-cements Ca-chloride is added (=accelerator; required to achieve a practical hydration time).

TABLE 2

Composition in % of the specific materials

| Material | CA | CS | $ZrO_2$ | Other additives |
|---|---|---|---|---|
| 1 | 65 mono CA (synthesized) | — | 35 (Porous powder - synthesized at 1300° C.) | Polycarboxylic compound, 4% molecular weight approx 20000 |
| 2 | — | 85 C3S (synthesized) | — | $CaCl_2$, 15% |

The paste was formed via mixing of the precursor liquid and precursor powder, the cement to liquid to ratio was close to 0.44. The components added to the liquid promotes a high cohesiveness of the paste. This means that the paste is easily kept together during injection thus avoiding, e.g. phase separation. This also reduces the risk of uncontrolled spread of the paste into undesired voids when injected.

The drug is in the above cases introduced in two different ways, A and B. In the first experiment A, the drug was introduced in the precursor material by dry mixing. The liquid was applied to the powder, and an injectable paste was achieved by homogeneous mixing in a shaker, e.g. a Rotomix. This paste was hydrated for 1 hour at 37° C. before it was release-tested in a phosphate buffer solution of 37° C. for 2, 8, 16 and 24 hours. The amount of test drug was 6 mg per 200 mg total carrier/implant material.

In the second experiment B, the drug was introduced in just the inert $ZrO_2$-phase with mean pore diameter of 0.5 micrometer by vacuum infiltration. The $ZrO_2$ powder was dried before it was mixed with the cement phase. The liquid was applied to the powder, and an injectable paste was achieved by homogeneous mixing in a shaker, e.g. a Rotomix. This paste was hydrated for 0.5 hour at 37° C. before it was release-tested in a phosphate buffer solution of 37° C. for 2, 8, 16 and 24 hours. The amount of test drug corresponded to 3 mg per 200 mg total carrier/implant material.

In all release tests, the release was measured by HPLC.

Below is presented the time-dependence of the slow release.

TABLE 3

The drug release with time (in mg)

| | Release Time | | | |
|---|---|---|---|---|
| Material | 2 h | 8 h | 16 h | 24 h |
| Material 1 - A | 0.5 | 2.2 | 4.0 | 5.8 |
| Material 1 - B | 2.5 | 2.7 | 2.9 | 3.0 |
| Material 2 - A | 0.4 | 2.1 | 4.1 | 5.9 |
| Material 2 - B | 2.7 | 2.8 | 2.9 | 3.0 |

From Table 3 it is clearly demonstrated the relatively rapid release from the porous oxide, while the chemically bonded phases contributes to a prolonged release time. The latter is also close to a constant release rate. The chemically bonded phases exhibit almost constant release, while the materials loaded in just the oxide exhibit a rapid release of all most all the drug loaded.

The invention claimed is:

1. An injectable ceramic paste for drug delivery in a subject, comprising:
   i) a ceramic precursor powder comprising
      a hydraulic non-hydrated calcium aluminate and/or calcium silicate phase (CBC phase), having a particle size of below 5 µm,
      a resorbable or stable phase comprising porous hydrated chemically bonded ceramics and/or oxides, having a granule size of 500 µm, open porosity in a range of 10-40 vol %, and an average pore size of 0.01-5 µm, and
      optional additives;
   ii) an effective amount of a pharmaceutical agent for drug delivery; and
   iii) a water-based hydration liquid, in a water to ceramic precursor powder ratio of 0.20-0.50,
   said paste forming an injectable paste capable of being injected into the subject, and forming a chemically bonded ceramic drug carrier material comprising the pharmaceutical agent upon hydration of the hydraulic phase after being injected into the subject.

2. The ceramic paste according to claim 1, wherein the non-hydrated calcium aluminate and/or calcium silicate phases are selected from CA, C3A, C12A7 and C3S.

3. The ceramic paste according to claim 1, wherein the ceramic precursor further comprises calcium aluminates, calcium silicates, calcium phosphates, calcium sulphates and Portland cement, and/or hydroxyapatite.

4. The ceramic paste according to claim 1, wherein the resorbable or stable phase comprising porous hydrated chemically bonded ceramics and/or oxides has a granule size of 100-300 µm.

5. The ceramic paste according to claim 1, wherein the ceramic precursor comprises a biocompatible phase that imparts radio-opacity.

6. The ceramic paste according to claim 5, wherein said biocompatible phase is selected from $ZrO_2$, Sr- and Ba-containing glasses.

7. The ceramic paste according to claim 1, wherein the ceramic precursor comprises hydroxyapatite.

8. The ceramic paste according to claim 1, wherein the ceramic precursor comprises a buffer system.

9. The ceramic paste according to claim 8, wherein the buffer system comprises hydrogen phosphates and/or acid salts.

10. The ceramic paste according to claim 1, wherein the pharmaceutical agent is selected from pain relief drugs, antiphlogistics, drugs for cancer/tumour treatment, vascular treatment, bone restoration, antibacterial and anti-inflammatory agents, antifungal agents, antivirus agents, analgesics, anticonvulsants; bronchodilators; antidepressants, auto-immune disorder and immunological disease agents, hormonal agents, TGB-beta, morphogenic protein, trypsin-inhibitor, osteocalcine, calcium-binding proteins (BMP), growth factors, Bisphosphonates, vitamins, hyperlipidemia agents; sympathetic nervous stimulants; oral diabetes therapeutic drugs; oral carcinostatics; contrast materials, radiopharmaceuticals, peptides, enzymes, vaccines and mineral trace elements or other specific anti-disease agents, as well as combinations of said agents.

11. The ceramic paste according to claim 1, wherein the ratio between the ceramic precursor powder and the water-based hydration liquid deviates at most +/−10% from the amount required for complete hydration of the CBCs.

12. A chemically bonded ceramic drug carrier material comprising the ceramic paste defined in claim 1, in cured form.

13. The chemically bonded ceramic drug carrier material according to claim 12, wherein the material exhibits an open porosity of 10-25 vol % and an average pore canal size of less than 10 nanometers.

14. The chemically bonded ceramic drug carrier material according to claim 12, wherein the CBC hydrates form crystal size of approximately 20-50 nanometers.

15. The chemically bonded ceramic drug carrier material according to claim 12, wherein the material sets in 2-10 minutes.

16. The chemically bonded ceramic drug carrier material according to claim 12, wherein 50% of the CBC phase hydrates in 1 hour.

17. The chemically bonded ceramic drug carrier material according to claim 12, wherein 90% of the CBC phase hydrates in 24 hours.

18. The chemically bonded ceramic drug carrier material according to claim 12, wherein the pH in the material is 5-9 during curing.

19. A method of manufacturing a chemically bonded ceramic material suitable for production of medical or orthopaedic implants, dental filling materials or dental implants, and a carrier material for medical agents in drug delivery, comprising mixing the ceramic precursor powder defined in claim 1 and the water-based hydration liquid, in a water to ceramic precursor powder ratio of 0.20-0.50.

20. The method according to claim 19, wherein a drug or medical agent is incorporated during the manufacturing, and wherein said drug or medical agent is selected from pain relief drugs, antiphlogistics, drugs for cancer/tumour treatment, vascular treatment, bone restoration, antibacterial and anti-inflammatory agents, antifungal agents, antivirus agents, analgesics, anticonvulsants; bronchodilators; antidepressants, auto-immune disorder and immunological disease agents, hormonal agents, TGB-beta, morphogenic protein, trypsin-inhibitor, osteocalcine, calcium-binding proteins (BMP), growth factors, Bisphosphonates, vitamins, hyperlipidemia agents; sympathetic nervous stimulants; oral diabetes therapeutic drugs; oral carcinostatics; contrast materials, radiopharmaceuticals, peptides, enzymes, vaccines and mineral trace elements or other specific anti-disease agents, as well as combinations of said drugs.

21. The method according to claim 20, wherein the drug is added to the hydration liquid.

22. The method according to claim 20, wherein the drug is mixed with the precursor powder.

23. The method according to claim 20, wherein the drug is mixed with or loaded into an additive.

24. The method according to claim 20, wherein the drug is enclosed in the open porosity of the hydrated phases.

25. The method according to claim 19, wherein viscosity-controlling additives selected from one or more of carboxylic acids, polymerised carboxylic acids, thickening agents, and superplasticisers are added.

26. A drug carrier implant comprising the ceramic paste defined in claim 1.

27. The drug carrier implant according to claim 26, wherein said drug carrier implant comprises a pharmaceutical agent selected from pain relief drugs, antiphlogistics, drugs for cancer/tumour treatment, vascular treatment, bone restoration, antibacterial and anti-inflammatory agents, antifungal agents, antivirus agents, analgesics, anticonvulsants; bronchodilators; antidepressants, auto-immune disorder and immunological disease agents, hormonal agents, TGB-beta, morphogenic protein, trypsin-inhibitor, osteocalcine, calcium-binding proteins (BMP), growth factors, Bisphosphonates, vitamins, hyperlipidemia agents; sympathetic nervous stimulants; oral diabetes therapeutic drugs; oral carcinostatics; contrast materials, radiopharmaceuticals, peptides, enzymes, vaccines and mineral trace elements or other specific anti-disease agents, as well as combinations of said agents.

28. A medical or orthopaedic implant comprising the ceramic paste defined in claim 1.

29. A dental filling material or dental implant comprising the ceramic paste defined in claim 1.

30. A kit for manufacturing the chemically bonded ceramic drug carrier material according to claim 12, comprising a container wherein the precursor powder and the water-based hydration liquid are stored separately in the container.

* * * * *